United States Patent [19]
Itoh et al.

[11] Patent Number: 5,876,709
[45] Date of Patent: Mar. 2, 1999

[54] OPHTHALMIC COMPOSITION CONTAINING ACTIVE VITAMIN D

[75] Inventors: Seiji Itoh, Mobara; Yasuo Ishii, Kawaguchi; Katsuhiko Mukai, Kashiwa; Kiyoshi Kita, Tokyo, all of Japan

[73] Assignee: New Vision Co., Ltd., Tokyo, Japan

[21] Appl. No.: 863,425

[22] Filed: May 27, 1997

[51] Int. Cl.⁶ .............................. A61K 9/127; A61K 9/14; A61K 31/74
[52] U.S. Cl. ........................ 424/78.04; 424/450; 424/489; 514/912
[58] Field of Search .................. 424/78.04, 450, 424/489; 514/912

[56] References Cited

U.S. PATENT DOCUMENTS 5,622,982  4/1997  Schuster et al. ........................ 514/399

FOREIGN PATENT DOCUMENTS

WO 98/18468  5/1998  WIPO .

*Primary Examiner*—Carlos A. Azpuru
*Attorney, Agent, or Firm*—Oblon, Spivak, McClelland, Maier & Neustadt, P.C.

[57] ABSTRACT

An ophthalmic composition for preventing corneal haze and corneal refraction anomaly observed after anterior ocular tissues are damaged or during corneal diseases comprises, as an effective component, vitamin D such as ergocalciferols and cholecalciferols or active vitamin D.

11 Claims, No Drawings

OPHTHALMIC COMPOSITION CONTAINING ACTIVE VITAMIN D

TECHNICAL FIELD

The present invention relates to an ophthalmic composition containing active vitamin D, an ultraviolet screening agent and an anti-allergic agent administered locally.

More specifically, the present invention pertains to an opthalmic composition for inhibiting or preventing corneal haze/opacity and corneal refraction anomaly due to hyperplasia in corneal tissues and hence the excess production of cellular materials deposited in the tissues developed after any corneal damage and during suffering from corneal diseases; an ophthalmic composition for shielding harmful ultraviolet rays; an agent intraocularly administered for controlling the activity of the ophthalmic cells, which is used during ophthalmic operations; an ultraviolet screening agent for protecting the skin from harmful ultraviolet light rays; and an anti-allergic agent intraocularly and locally administered.

PRIOR ART

Rachitis is one of the osteopathy, it has formerly been believed that the rachitis is closely related to the action of the sunlight. Thereafter, however, it has been found out that a certain vitamin is closely involved in the rachitis. This anti-rachitis vitamin is named vitamin D. Vitamin $D_2$ obtained by purifying vitamin $D_1$ which is a mixture with other isomers as well as vitamin $D_3$ discovered through the subsequent studies have widely been used in the treatments of many patients suffering from osteopathy such as rachitis, osteomalacia, osteoporosis, ostitis fibrous and osteosclerosis, malignant tumors such as breast cancer and carcinoma of large intestine, as well as dermatosis such as psoriasis. In general, the term "vitamin D" means vitamin $D_2$ (ergocalciferol) and vitamin $D_3$ (cholecalciferol) exhibiting a high anti-rachitis activity and therefore, this term is also used in the explanation of the present invention according to this definition.

The ultraviolet absorption spectra of vitamin D and their active forms in general show an absorption peak around 265 nm (molar extinction coefficient: about 18,000). For instance, ergocalciferol, 25-monohydroxy vitamin $D_2$, $1\alpha$, 25-dihydroxy vitamin $D_2$, 24, 25-dihydroxy vitamin $D_2$ and the like have ultraviolet absorption spectra possessing an absorption peak at about 265 nm (molar extinction coefficient: about 18,900).

In addition to the foregoing vitamin D's, provitamin D's and previtamin D's also have ultraviolet absorption spectra similar to those of the former. Ergosterol and 7-dehydrocholesterol as provitamin D's show ultraviolet absorption spectra possessing absorption peaks at 271, 281 and 293 nm (molar extinction coefficient: 11,000 and 10,920 respectively). In addition, pre-ergocalciferol and cholecalciferol as previtamin D's show ultraviolet absorption spectra possessing absorption peaks at 260 nm (molar extinction coefficient: 9, 000).

Vitamin D is an essential vitamin for the bone modeling and it is prescribed by the Ministry of Public Welfare that the required amount of this nutrient to be taken with foods is set at 200 IU (5 μg)/day. However, the required amount of the nutrient differs from that prescribed in foreign countries (i.e., 400 IU/day) because of the presence of vitamin D, which is produced in the skin by the action of ultraviolet light rays through sunbathing. In other words, it is necessary to take excess of vitamin D in case where sufficient sunbathing is not ensured. Vitamins $D_2$ to $D_7$ are classified as vitamins having rachitic-inhibitory activity, but presently used in the treatment thereof are vitamin $D_2$ and vitamin $D_3$ having high physiological activities.

Vitamin D's are administered to patients per oral route or by injection. In case of skin diseases, they are also administered in the form of ointments. It has been known that the vitamin D undergoes a change in its molecular structure through the action of ultraviolet rays or in the liver and kidney and that it is thus converted into active vitamin D having high biological activities. It has been recognized that vitamin D's have not only a calcium-regulatory effect, but also other biological activities since the discovery of the active vitamin $D_3$, i.e., calcitriol ($1\alpha$, 25-dihydroxy cholecalciferol) as a derivative of the cholecalciferol. As other derivatives or analogues of the cholecalciferol, there have been known, for instance, alpha-calcidol ($1\alpha$-monohydroxy cholecalciferol) and calcifedol (25-monohydroxy cholecalciferol). There have presently been known about 16 kinds of cholecalciferol derivatives. In addition, there have been developed several kinds of cholecalciferol analogues such as OCT (22-oxacalcitriol) and calcipotriol. The presence of active vitamin D receptors in cells has been discovered and there have been conducted studies on inhibition of cell activities because of the ability of the active vitamin D's to control the production of various cytokines.

In the field of the ophthalmology, it has been known, as the symptoms caused due to vitamin deficiency, for instance, night blindness and xerophthalmia due to vitamin A deficiency; beriberi and weak eyesight because of vitamin $B_1$ deficiency; superficial punctate keratitis because of the vitamin $B_2$ deficiency (sometimes associated with retroocular neuropapillitis and optic atrophy); and scorbutus due to the vitamin C deficiency (wherein there are often observed bleeding in eyelids, conjunctivae and retinae).

Dr. Ohashi et al. in Osaka University studied the inhibitory effect of vitamin $D_3$ against the expression of MHC class antigens in order to suppress any rejection observed during the keratoplasty and suggest that vitamin $D_3$ may serve to control the rejection of the transplantation of cornea (Bulletin of Ophthalmologic Society in Japan, 1990, Vol. 94, an extra edition, p. 250).

Japanese Un-Examined Patent Publication No. Hei 3-24016 discloses studies of cultivation of human glia cells wherein the ability of active vitamin $D_3$ to inhibit the proliferation of glia cells and also suggests that active vitamin $D_3$ may be applied to the treatment of patients suffering from proliferative retinopathy.

Japanese Examined Patent Publication No. Hei 4-43887 discloses that active vitamin $D_3$ is effective for the treatment of cataract such as congenital cataract, senile cataract, complicated cataract and diabetic cataract.

U.S. Pat. No. 5,254,538 discloses that vitamin D compounds are effective in healing of wounds and healing of a variety of ulcers.

The surgical operation with a scalpel has been employed for the correction of short-sightedness and astigmatism, but this would adversely affect the visual power. For instance, the operated eye proceeds to the over correction after the operation and the incised site of the cornea becomes turbid or irregular reflection which impair the visual acuity.

As laser devices for operating cornea, there have been known an excimer laser and an Ho:YAG laser. The laser operations for cornea are divided into the operations for healing diseases and those for correcting the visual power.

Glaucoma is a disease in which an abnormality is observed in the circulation-control mechanism of the aqueous humor filling up the anterior chamber, i.e., the space formed between the cornea and the lens, this leads to an increase in the volume of the aqueous humor and in turn a high intraocular pressure disease and consequently, leads to the visual field defect and even to loss of eyesight because of the compulsion and contraction of the papillae of the optic nerve. In case where the high intraocular pressure disease cannot be relieved by the chemotherapy using an epinephrine preparation or a β-blocker, there has been adopted a therapy which comprises a surgical operation for forming passages through which the aqueous humor flows out from the space. The operation for excising the trabecular meshwork as a typical operation of glaucoma comprises slicing the sclera, the outer shell of the eye ball, into the outer and the inner layers and then partially excising the inner layer of the sclera and the outer periphery of the anterior chamber to thus form a passage which permits the communication between the inside and outside portions of the eye ball and through which the aqueous humor can flow out. After such an operation, however, the passage is occluded since fibroblasts produce extracellular matrix and fill up the excised site. A non-selective cell-inhibitory agent such as mitomycin or 5-FU is used as a fibroblast activity-inhibitory agent in order to prevent the plugging of the passage, but this is often accompanied by severe complications such as perforation of sclera due to necrosis of the scleral tissue and intraocular infections due to the inhibition of the host defense against infection.

The corneal degeneracy (corneal distrophia) is a disease which causes the keratoleukoma due to the metabolic deficiency of corneal tissues, which leads to deposition of phospholipids and mucopolysaccharides in the keratocytes. As corneal degeneracies, there have been known, for instance, granular corneal degeneracy, porphyritic corneal degeneracy, cancellated corneal degeneracy, colloidal-guttate corneal degeneracy, Schneiderian corneal degeneracy and Francois corneal degeneracy and as degeneracies of endothelium, there have been known, for instance, Fuchs' cornea-endothelial degeneracy. On the other hand, the corneal ulcer is a disease wherein the keratocyte produces an excess of the collagenase to thus form an ulcer. Accordingly, the corneal degeneracy and the corneal ulcer are completely different from one another in causes of their crisis and clinical symptoms.

In the patient who has been subjected to an operation for excision of cornea with an excimer laser, there is observed, after the operation, the occurrence of hyperplasia in the cells during the process for healing the damaged corneal tissues and further there are sometimes observed reduction in the degree of transparency and a change in the refractive power due to the presence of cellular products. The normal epithelial cell of the cornea in general comprises about 5 layers, but when the traumatic injury reaches even the keratocyte and it is complicatedly damaged, the corneal endothelial cells covering the keratocyte may sometimes run up to about 10 layers. The damaged corneal cells undergo hyperplasia and produce metabolites such as collagen and/or proteoglycans to thus undergo restoration. The multilayered epithelial cells will be converted into the normal layers in the future, but the refractive power and the transparency of the cornea are influenced by the transient hyperplasic in the epithelium and the excess production of the cellular materials observed during the wound-healing process. Moreover, a steroid drug is administered after the operation for excision of cornea with the excimer laser, but it has been known that this is accompanied by steroid glaucoma (high intraocular pressure disease), steroid cataract and infectious diseases as side effects.

The cataract surgery comprises removing the lens which has become turbid and an operation for transplanting an artificial lens (intraocular lens) is in general used in combination with the excision. The usual procedure comprises incising the epithelial cells on the front face of the capsule of lens to thus excise only the contents (the parenchyma of the lens) thereof, then inserting an intraocular lens into the remaining lens capsule and fixing the lens thereto. The epithelial cells remaining on the front face of the lens deposit capsule gradually undergo proliferation and spreading and extracellular matrix such as collagen. Subsequently, fibrin, iridal pigmentary epithelial cells and/or macrophages exuded in the aqueous humor are adhered to the deposits to thus form turbid and denatured membranous tissues. The transparency of cornea may sometimes be reduced by the coverage of the rear face of the lens capsule and the intraocular lens surface with such a membrane and may lead to reduction of the visual power of the patient after the operation. Moreover, astigmatism has often been observed after the cataract surgery. It has been recognized that this is because a nonuniformly distributed tensile force is applied to cornea due to the scar tissues formed by the hyperplasia of cells and/or excess production of extracellular matrix during the healing process of the incised wound formed on the cornea or sclera in the proximity to the outer periphery of cornea for the sake of the operation and therefore, the shape of the cornea is deformed or strained. It has been believed that the two-rank-reduction in the visual acuity is observed on about 10% of the patients suffering from cataract after one year from the operation and on about 20% of the patients after two years from the operation.

As methods for preventing cornea from becoming turbid after operations, there have conventionally been in course of studies or there have practically been applied, for instance, a method in which the lenticular epithelial cells are removed mechanically or by a cytotoxin which can specifically affect the epithelial cells; a method for inhibiting the outgrowth of the lenticular epithelial cells by devising the shape of the intraocular lens to be transplanted; and a method for inhibiting the activity of the lenticular epithelial cells by administering, for instance, an anti-inflammatory agent or an inhibitory agent for cellular metabolism after the operation. However, there has not yet been developed any safe and effective method.

The foregoing are examples in the field of ophthalmology, which are accompanied by several problems concerning the operation of the anterior ocular region.

It has been well-known that ultraviolet rays are harmful to the skin and eyes. In particular, the ultraviolet rays whose wavelength falls within the range of from 200 to 315 nm would become a cause of inducing sunburn, stains, freckles and keratitis and it has in general been recognized that the ultraviolet rays having a wavelength of about 260 nm, among others, would become a cause of inducing teratogeny and oncogenesis such as skin cancer in the usual cells. The formation of a pterygium in the anterior ocular region is considered to be a disease in which ultraviolet rays are involved, in addition to the corneal diseases including keratitis. However, there has never been known any UV screening agent which is permitted to use in the eyes or the region in the proximity thereto. In this respect, however, ultraviolet rays having a wavelength of 254 nm is currently used in the ultraviolet stelirizer.

In addition, vitamin K has an effect of activating blood coagulation factors and the relation between vitamin K and metabolism of bones has been investigated recently. Moreover, it has also been reported that vitamin K can enhance the ability of vitamin $D_3$ to metabolize bones. Vitamin K is soluble in oils and has an ultraviolet absorption spectra falling within the range of from 240 to 270 nm. Vitamin $K_1$ has a molecular weight of 450.7 and UV absorption peaks in the region ranging from 242 to 269 nm and at 325 nm, vitamin $K_2$ (menaguinone 4, 6 or 7) is a menaquinone whose side chain comprises a repeated isoprene residue and has a molecular weight ranging from 444.7 to 649.0 and UV absorption peaks in the regions ranging from 243 to 270 nm and 325 to 328 nm.

The number of patients suffering from allergic conjunctivitis, which has not been noticed conventionally, is increased recently. As causes therefor, there has been listed, for instance, an increase in allergens such as pollinosis causative allergens and changes in physical constitution. Further it has been recognized that the keratoconjunctivitisicca (dry eye) may be involved in this disease as a cause therefor. It has been known that, if suffering from dry eye, the secretion of the lacrimal fluid is reduced, foreign substances such as pollens cannot sufficiently be washed away by the fluid and accordingly, such an allergic reaction is liable to occur. Various phenomena other than the pollinosis such as contact lenses, photochemical smog and smoke may possibly be considered to be involved in these allergic ophthalmic diseases. It has been difficult to immediately cure any local allergic reaction in the eyes, in case of the allergic diseases observed in the ophthalmology such as pollinosis, allergic conjunctivitis and vernal keratoconjunctivitis, and steroid-containing eye drops has presently been administered as a symptomatic treatment. The steroid-containing eye drops provide strong antiinflammatory action and anti-allergic action, while it has been known that the eye drops also have severe side effects such as the recurrence of glaucoma and corneal herpes and infection with fungi. As anti-allergic agent, there have been used, for instance, sodium cromoglycate, tranilast and ketotifen and there have been administered antihistamic agents per oral route.

In, for instance, pollinosis due to the pollens of Cryptomeria japonica (sugi), the pollens in general enter into the eyes, easily absorb water and get swollen when coming in contact with tear, followed by the breakage of the outer shell and release of components of the pollens. The released pollen components finally reach the conjunctival subepithelial region. Immunoglobulin E (IgE) antibody specific to the sugi pollens undergoes an immunoreaction with the components (antigen-antibody reaction) in the conjunctival subepithelial region, chemotransmitters such as histamin present in mast cells are correspondingly released and delivered to the blood vessel and neuroterminals of conjunctiva and thus results in the symptoms such as itching of the eyes, hyperemia, secretion of lacrimal fluid and eye mucus.

DISCLOSURE OF THE INVENTION

Accordingly, a first object of the present invenion is to provide an ophthalmic composition which can prevent the occurrence of corneal haze/opacity and corneal refraction anomaly accompanied by the scar formation developed after cornea or anterior ocular tissues including the sclera near the outer periphery of the cornea are damaged.

A second object of the present invention is to provide an ophthalmic composition capable of preventing any occurrence of corneal haze/opacity and corneal refraction anomaly observed when suffering from corneal diseases.

A third object of the present invention is to provide an ophthalmic composition for protecting the eye ball tissues from harmful ultraviolet rays.

A fourth object of the present invention is to provide a UV screening agent capable of protecting the skin from the irradiation with the most harmful ultraviolet rays of about 260 nm in wavelength.

A fifth object of the present invention is to relieve any impaired vision due to inhibited intraocular transparency including high intraocular pressure disease caused by, for instance, proliferation, outgrowth and migration of cells in intraocular tissues, inhibition of hyperplasia of chemotransmitters and excess production of cellular materials caused by operative invasion during ophthalmic operation. More specifically, the fifth object of the present invention is to provide a preventive agent for the impaired vision which has almost no side effect and can be administered during ophthalmic operation, since the administration of a steroid agent as a presently adopted symptomatic treatment suffers from a problem of side effects.

A sixth object of the present invention is to control the cellular activities in intraocular tissues responding to operative invasion during ophthalmic operations, without any time lag.

A seventh object of the present invention is to provide an ophthalmic anti-allergic agent for preventing or treating allergic diseases in the field of ophthalmology such as pollinosis, allergic conjunctivitis and vernal keratoconjunctivitis and more specifically, to provide an ophthalmic anti-allergic agent which has almost no side effect, since the administration of a steroid agent as a presently adopted symptomatic treatment suffers from a problem of side effects.

The inventors of this invention have conducted various studies to accomplish the foregoing objects, have found out that the use of active vitamin D is effective for achieving the foregoing objects and thus have completed the present invention.

According to a first aspect of the present invention, there is provided an ophthalmic composition for preventing corneal haze/opacity and corneal refraction anomaly developed after anterior ocular tissues are damaged, which comprises, as an effective component, at least one member selected from the group consisting of ergocalciferols and cholecalciferols.

According to a second aspect of the present invention, there is provided an ophthalmic composition for preventing corneal haze/opacity and corneal refraction anomaly observed when suffering from corneal diseases, which comprises, as an effective component, at least one member selected from the group consisting of ergocalciferols and cholecalciferols.

According to a third aspect of the present invention, there is provided an ophthalmic composition for protecting the eye ball tissues from harmful ultraviolet rays, which comprises, as an effective component, at least one member selected from the group consisting of ergocalciferols, cholecalciferols, active vitamin D's carrying a hydroxyl group on one or both of the C1 position on the sterol A ring and the C25 position on the side chain, oxacalcitriol, calcipotriol and dihydrotachysterol.

According to a fourth aspect of the present invention, there is provided an ophthalmic composition for protecting the ophthalmic tissues from harmful ultraviolet rays, which comprises, as an effective component, vitamin K.

According to a fifth aspect of the present invention, there is provided a UV screening agent which is locally administered to the skin and which comprises, as an effective component, at least one member selected from the group consisting of provitamin D, previtamin D, vitamin D, active vitamin D, active vitamin D analogues, vitamin K and vitamin K analogues.

According to a sixth aspect of the present invention, there is provided an anti-allergic agent to be locally administered which comprises, as an effective component, at least one member selected from the group consisting of ergocalciferols, cholecalciferols, active vitamin D's carrying a hydroxyl group on one or both of the C1 position on the sterol A ring and the C25 position on the side chain, vitamin $D_2$ analogues, vitamin $D_3$ analogues, active vitamin $D_2$ analogues and active vitamin $D_3$ analogues.

According to a seventh aspect of the present invention, there is provided an agent intraocularly administered for controlling the cellular activities in intraocular tissues caused by ophthalmic operations, which comprises, as an effective component, at least one member selected from the group consisting of ergocalciferols, cholecalciferols, active vitamin D derivatives each carrying a hydroxyl group on one or both of the C1 position on the sterol A ring and the C25 position on the side chain, vitamin $D_2$ analogues, vitamin $D_3$ analogues, active vitamin $D_2$ analogues and active vitamin $D_3$ analogues.

BEST MODE FOR CARRYING OUT THE INVENTION

The first aspect of the present invention relates to an ophthalmic composition for preventing corneal haze/opacity and corneal refraction anomaly observed after anterior ocular tissues are damaged, which comprises, as an effective component, at least one member selected from the group consisting of ergocalciferols and cholecalciferols and the second aspect of the present invention relates to an ophthalmic composition for preventing corneal haze/opacity and corneal refraction anomaly observed when suffering from corneal diseases, which comprises, as an effective component, at least one member selected from the group consisting of ergocalciferols and cholecalciferols.

In the patient who has been subjected to an operation of cornea, there is observed, after the operation, the occurrence of hyperplasia in the cells during the process for healing the damaged corneal tissues and further there are sometimes observed reduction in the degree of transparency and a change in the refractive power due to the presence of cellular materials. The normal corneal epithelium in general comprises about 5 layers, but when the traumatic injury reaches even the stroma of cornea and it is complicatedly damaged, the cornea-epithelial cells covering the stroma may sometimes run up to about 10 layers. The damaged corneal cells undergo hyperplasia and produce cellular materials in excess to thus accelerate the restoration. The multilayered epithelium will return to the normal structure in the future, but the refractive power and the transparency of the cornea are influenced by the transient hyperphasia in the epithelium and the cellular material produced by the epithelial cells as well as the stroma cells during the wound healing process. Moreover, a steroid drug is administered after the operation for cornea, but it has been known that this is accompanied by steroid glaucoma and steroid cataract as side effects.

As operations for restoring damaged cornea and ophthalmic operations which causes a traumatic injury of the anterior ocular region, there have been known, for instance, correction of corneal refraction, the cataract surgery, intraocular lens transplantation, operations for pterygium, operations for removing foreign body in the cornea, corneal transplantation, keratoplasty and operations for glaucoma.

In the patients suffering from corneal diseases, the cells present in inflammatory sites undergo hyperplasia and there are sometimes observed reduction in the degree of transparency and a change in the refractive power of the cornea due to the presence of cellular materials. The cellular materials are produced excessively under inflammatory condition. There have also been known corneal diseases such as corneal ulcer and corneal degeneracy which are caused by cellular materials such as collagenase, extraordinary type of proteoglycans and amyloid derived from corneal epithelial cells and keratocytes, although these diseases do not relate to inflammatory conditions. The deposited materials affect the refraction and transparency of the cornea. It has also been known that the steroid drugs are not often effective for the treatment of corneal diseases caused by the cellular materials such as collagenase and the extraordinary cellular products. Collectively, examples of corneal diseases include, for instance, keratitis, corneal ulcers and corneal degeneracy.

The ophthalmic composition of the present invention makes the most use of the cell proliferation-inhibitory effect and the cell differenciation-inducing effect and is directly administered to the eyes of patients whose anterior ocular region is damaged and who suffer from corneal diseases to thus hold the transparency of the cornea and the normal refraction thereof and in turn prevent any reduction of visual functions of the eyes. Preferred ophthalmic compositions according to the present invention are solutions containing ergocalciferol and/or cholecalciferol.

The present invention makes the most use of the following fact as a means for solving the foregoing problems. That is, the fibroblasts derived from the keratocytes and those persist in the anterior ocular tissues may possess enzymes involved in the conversion of administered vitamin D into its active form. More specifically, the administered vitamin D may be substituted with hydroxyl groups on either or both of the C1-position on the sterol A ring and the C25-position of the side chain thereof by the action of the enzyme of the mitochondria or microsome in the fibroblasts which are active and thus the former is converted into its active form. The active vitamin D derivative in which only one of the C1-position on the sterol A ring and the C25-position of the side chain thereof is substituted with a hydroxyl group is substantially weaker than the 1α, 25-dihydroxy vitamin D wherein the both positions are substituted with hydroxyl groups and which has the highest biological activity such as cytokine-inhibitory activity and differenciation-inducing effect, but may still retain biological activity to some extent. The amount of the active form thus converted depends on the abundancy of the fibroblasts. In other words, the inventors have found out that the rate of conversion of vitamin D into its active form would be increased only when the damaged anterior ocular site is in the inflammatory condition and the fibroblast becomes active.

In the patient who has been subjected to a corneal operation, the number of fibroblast distinctly increases in the stroma. In order to prevent any change in refractive power of the cornea and corneal haze/opacity caused by the increase of the fibroblast, the ophthalmic composition of the present invention which comprises vitamin D as an effective component is accordingly instilled in the eyes immediately after the operation to thus inhibit the activity of the corneal epithelial cells and keratocytes, to suppress the hyperplasia of the corneal epithelial cells and keratocytes, which are in the inflammatory conditions, and any excess production of the cellular materials thereof through the foregoing activity-inhibition and to thus prevent any reduction of the visual power due to change in the refractive power of the cornea and the corneal haze/opacity.

If the ophthalmic composition of the present invention which comprises vitamin D as an effective component is administered to patients suffering from corneal diseases, the composition can inhibit accumulation of inflammatory cells and can correspondingly prevent reduction of the degree of transparency and insufficient refraction of the cornea due to cellular materials in case of keratitis. In respect of corneal diseases caused by collagenase and other extraordinary type of cellular materials, the ophthalmic composition of the present invention which comprises vitamin D as an effective component can inhibit the collagenase-producing ability of the keratocyte in case of corneal ulcer or normalize the extraordinary cellular materials producing cells in case of corneal degeneracy to thus heal these corneal diseases such as ulcer and corneal degeneracy.

The present invention has been completed on the basis of such a finding that the optical transparency and refractive characteristics of cornea can be normalized if a composition obtained by incorporating oil-soluble vitamin D into an ophthalmic physiological buffer is locally administered to the human eyes of patients suffering from corneal diseases. In the present invention, vitamin D or active vitamin D may be dispersed or dissolved in an ophthalmic physiological buffer containing ethanol or a surfactant as a solubilizing agent to thus give an ophthalmic composition. It is also possible to dissolve vitamin D or active vitamin D in a vegetable oil such as sesame oil to give an ophthalmic composition since vitamin D is soluble in oil.

If the ophthalmic composition of the present invention is dropped in the eyes whose anterior ocular region has been damaged, vitamin D as the effective component thereof is converted into its active form by the action of an enzyme secreted by activated fibroblasts, the resulting active vitamin D binds to the receptors of cells in inflammatory conditions and present in proximity thereto and thus affects the DNA's of these cells to consequently inhibit the secretion of cellular products such as various kinds of cytokines and proteins. In other words, the present invention has been developed on the basis of such an idea that the fibroblast is not only a target cell for active vitamin D, but also an active vitamin D-producing cell.

Vitamin D or active vitamin D does not show any cytotoxicity and accordingly, it has been considered that vitamin D or active vitamin D does not affect normal cells at all. When dropping the ophthalmic composition of the present invention in the eyes, vitamin D does not easily reach the posterior ocular region. For this reason, it would be effective to orally administer the composition simultaneously with the dropping thereof in the eyes to effect the treatment of the posterior ocular region which may be required in the future. It is in general recognized that the smaller the molecular weight of the drug and the higher the hydrophobicity thereof, the higher the permeability of the cornea to drugs. Therefore, vitamin D or active vitamin D has a good ability of permeating the cornea. For instance, the molecular weight of cholecalciferol is 384.6 dalton.

The concentration of vitamin D as the effective component in the ophthalmic composition of the present invention suitably ranges from about 1 international unit (IU) (0.025 µg)/ml to about 2000 IU(50 µg)/ml, while that of active vitamin D therein suitably ranges from about 0.04 IU(1 ng)/ml to about 40 IU(1 µg)/ml. Preferably, the concentration thereof ranges from about 1 IU(0.025 µg)/ml to about 2000 IU(50 µg)/ml.

According to the third aspect of the present invention, there is provided an ophthalmic composition for protecting the eye ball tissues from harmful ultraviolet rays, which comprises, as an effective component, at least one member selected from the group consisting of ergocalciferols, cholecalciferols, active vitamin D's carrying a hydroxyl group on one or both of the C1 position on the sterol A ring and the C25 position on the side chain, oxacalcitriol, calcipotriol and dihydrotachysterol.

According to the fourth aspect of the present invention, there is provided an ophthalmic composition for protecting the ophthalmic tissues from harmful ultraviolet rays, which comprises, as an effective component, vitamin K.

The vitamin D or active vitamin D is included in the tear film covering the ocular surface and accumulated in the cornea and/or conjunctiva when administering the ophthalmic composition of the present invention and as a result, significantly absorbs harmful ultraviolet rays. The vitamin D or active vitamin D would be effective for preventing the occurrence of keratitis and the formation of pterygium. In addition, when abrading the corneal surface using an excimer laser, in particular, incising the Bowman's layer, ultraviolet rays may further be detrimental to the eyes. For this reason, the administration of the ophthalmic composition comprising vitamin D or active vitamin D would be effective for protecting ocular tissues from the action of detrimental ultraviolet rays.

Vitamin K is also oil-soluble and accordingly, included in the tear film and accumulated in the cornea and/or conjunctiva to thus significantly absorb detrimental ultraviolet rays like vitamin D or active vitamin D.

The concentration of vitamin D or active vitamin D in the ophthalmic composition of the present invention suitably ranges from about 1 IU(0.025 µg)/ml to about 2000 IU(50 µg)/ml for vitamin D and about 0.04 IU(1 ng)/ml to about 40 IU(1 µg)/ml for active vitamin D, because the composition is in general locally administered. Preferably, the concentration thereof ranges from about 1 IU(0.025 µg)/ml to about 2000 IU(50 µg)/ml therein suitably ranges from. When dropping the composition in the eyes, the amount of a drop of the composition is in general equal to about 20 µl. Suitably the concentration of vitamin K, in particular, vitamin $K_2$ likewise ranges from about 0.025 µg/ml to about 50 µg/ml, because the composition is locally administered.

The composition of the present invention is most preferably used in the form of an aqueous eye drop. However, it is also possible to encapsulate vitamin D, active vitamin D or vitamin K in an ophthalmic drug-delivery system such as liposome, microsphere, protein, collagen or soft contact lenses for treatment or to adhere such vitamin to the drug-delivery system to thus give an ophthalmic composition. The composition of the present invention may likewise be used in the form of a viscous ophthalmic solution prepared by admixing vitamin D, active vitamin D or vitamin K with at least one viscous base selected from the group consisting of, for instance, polyvinyl alcohol, methyl cellulose, hyaluronic acid, chondroitin sulfuric acid and collagen.

According to the fifth aspect of the present invention, there is provided a UV screening agent which is locally administered to the skin and which comprises, as an effective component, at least one member selected from the group consisting of provitamin D, previtamin D, vitamin D, active vitamin D, active vitamin D analogues, vitamin K and vitamin K analogues.

The present invention according to this embodiment makes the most use of such UV-absorption characteristics of vitamin D, active vitamin D, vitamin D analogues and vitamin K that they can absorb, as the maximum absorption peak, harmful UV rays around 260 nm and is characterized in that vitamin D or active vitamin D is formulated into an ophthalmic composition for use in protecting the eyes from detrimental ultraviolet rays. Suitable as effective components for the ophthalmic composition for protecting the ophthalmic tissues from detrimental ultraviolet rays are ergocalciferol and cholecalciferol as vitamin D; active vitamin D's each carrying a hydroxyl group on one or both of the C1 position on the sterol A ring and the C25 position on the side chain as active vitamin D; and dihydrotachysterol as a vitamin D analogue.

Specific examples of provitamin D, previtamin D, vitamin D, active vitamin D, active vitamin D analogues, vitamin K and vitamin K analogues as effective components for the UV screening agent of the present invention are ergosterol, 7-dehydrocholesterol, pre-ergocalciferol, pre-cholecalciferol, calcitriol (1$\alpha$, 25-dihydroxy vitamin D), 1 $\alpha$, 24-dihydroxy vitamin D, $\alpha$-calcidol (1$\alpha$-monohydroxy vitamin D), calcifedol (25-monohydroxy vitamin D), 1 $\alpha$, 24, 25-trihydroxy vitamin D, 1$\beta$, 25-dihydroxy vitamin D, oxycalcitriol, calcipotriol, dihydrotachysterol, vitamin $K_1$, vitamin $K_2$, and menadiol diphosphate (vitamin K analogue).

The UV screening agent of the present invention comprises, as an effective component, at least one member selected from the group consisting of provitamin D, previtamin D, vitamin D, active vitamin D, active vitamin D analogues, vitamin K and vitamin K analogues which are all oil-soluble and preferably comprises a cosmetic product or a sunburn-preventing agent and the foregoing component incorporated therein. The UV screening agent can prevent or relieve the effect of detrimental ultraviolet rays on the skin by locally applying the agent to the skin. More specifically, the UV screening agent of the present invention may be used in dosage forms such as ointments, creams, lotions and sprays. The concentration of provitamin D, previtamin D, vitamin D, active vitamin D, active vitamin D analogues, vitamin K or vitamin K analogues as the effective component of the UV screening agent of the present invention suitably ranges from 0.01 $\mu$g/ml(or $\mu$g/g) to 100 $\mu$g/ml(or $\mu$g/g), since the agent is locally administered.

Provitamin D, previtamin D, vitamin D, active vitamin D, active vitamin D analogues, vitamin K and vitamin K analogues do not show any cytotoxicity at all and therefore, they would not affect the epithelial cells of the skin so far as they are not used in any abnormal formulation. When the UV screening agent of the present invention is locally administered to the skin, the agent can prevent or relieve the effect of ultraviolet rays on the dermal tissues since provitamin D, previtamin D, vitamin D, active vitamin D, active vitamin D analogues, vitamin K or vitamin K analogues can absorb detrimental ultraviolet rays.

According to the sixth aspect of the present invention, there is provided an anti-allergic agent to be locally administered which comprises, as an effective component, at least one member selected from the group consisting of ergocalciferols, cholecalciferols, active vitamin D's carrying a hydroxyl group on one or both of the C1 position on the sterol A ring and the C25 position on the side chain, vitamin $D_2$ analogues, vitamin $D_3$ analogues, active vitamin $D_2$ analogues and active vitamin $D_3$ analogues.

The locally administered anti-allergic agent of the present invention preferably comprises oil-soluble vitamin D or active vitamin D incorporated into an ophthalmic physiological buffer and the agent can effectively prevent or relieve any allergic response in the palpebral conjunctiva, bulbar conjunctiva and the cornea of patients by directly administering it to the eyes thereof. Preferred examples thereof also include those obtained by diluting such an effective component with an ophthalmic physiological buffer while containing ethanol or a surfactant as a solubilizing agent or by dissolving the effective component in a vegetable oil such as sesame oil.

The concentration of the effective component in the locally administered anti-allergic agent suitably ranges from about one international unit (IU)(0.025 $\mu$g)/ml to 2000 IU(50 $\mu$g)/ml for vitamin D and about 0.04 IU(1 ng)/ml to 40 IU(1 $\mu$g)/ml for active vitamin D. The amount of one drop thereof when dropping in the eyes is in general equal to about 20 to 50 $\mu$l.

To make clear the effectiveness of the locally administered anti-allergic agent, experiments were carried out with experimental allergic conjunctivitis in guinea pigs which is a method currently used when examining the allergic response at a local part, i.e., eye in this case. In these experiments, there was used the method for inducing an allergic reaction reported by Shoji et al. of Nihon University at the 100-th Meeting of Japanese Ophthalmological Society. The results of these experiments indicate that the extent of infiltration and proliferation of, for instance, inflammatory cells and/or mast cells is low in the group to which the anti-allergic agent of the invention is administered through dropping and that the extent of the conjunctivitis is also low as compared with the control group free of the anti-allergic agent.

These results clearly demonstrate that the local and direct administration of vitamin D's to the eyes permits the inhibition of any allergic reaction in the eyes. Vitamin D's are highly safe and can be administered to the eyes so far as they are used in unreasonable concentrations. It can be considered that side-effects would not be recognized even if the anti-allergic agent of the invention is administered for a prolonged period.

Vitamin D, ergocalciferol, cholecalciferol or the like are likewise converted into active vitamin D by hydroxylases in conjunctiva which is in the initial stage of allergy or has fully developed inflammation, the resulting active vitamin D is incorporated into the cells in the proximity thereto such as conjunctival epithelial cells or mast cells in inflammatory conditions and exerts an influence on the cellular DNA to thus control the differentiation induction or to control the production of, for instance, various cytokines or other proteins. In other words, the cells in the conjunctiva may serve not only as target cells for active vitamin D, but also as vitamin D-producing cells and vitamin D and active vitamin D do not possess any cytotoxicity and accordingly, would not adversely affect the normal cells.

The anti-allergic agent of the present invention is most preferably used in the form of an aqueous eye drop. However, it is also possible to encapsulate vitamin D and/or active vitamin D in an ophthalmic drug-delivery system such as liposome, microsphere, protein gels, collagen or soft contact lenses for treatment or to adhere such vitamin to the drug-delivery system to thus give an ophthalmic composition. The anti-allergic agent of the invention may likewise be used in the form of a viscous ophthalmic solution prepared by admixing vitamin D and/or active vitamin D with at least one viscous base selected from the group consisting of, for instance, polyvinyl alcohol, methyl cellulose, hyaluronic acid, chondroitin sulfuric acid and collagen.

According to the seventh aspect of the present invention, there is provided an agent intraocularly administered for controlling the cellular activities in intraocular tissues during ophthalmic operations, which comprises, as an effective component, at least one member selected from the group consisting of ergocalciferols, cholecalciferols, active vitamin D derivatives each carrying a hydroxyl group on one or both of the C1 position on the sterol A ring and the C25 position on the side chain, vitamin $D_2$ analogues, vitamin $D_3$ analogues, active vitamin $D_2$ analogues and active vitamin $D_3$ analogues.

Examples of preferred effective components usable in the agent intraocularly administered for controlling the cellular activities in intraocular tissues according to the present invention include calcitriol (1 α, 25-dihydroxy vitamin $D_3$), 1α, 24-dihydroxy vitamin$D_3$, α-calcidol (1α-hydroxy vitamin $D_3$), calcifedol (25-hydroxy vitamin $D_3$), 1 α, 24, 25-trihydroxy vitamin $D_3$, 1 β, 25-dihydroxy vitamin $D_3$, 22-oxacalcitriol, calcipotriol, KH1060 (20(R)-22-oxa-24, 26, 27-trihomocalcitriol) and dihydrotachysterol.

The agent intraocularly administered for controlling the cellular activities in intraocular tissues is designed in such a manner that it is locally administered to the eyes during ophthalmic operations and the dosage forms thereof may be, for instance, injections to be intraocularly administered and those obtained by incorporating the agent into, for instance, viscoelastic substances, intraocular lenses, substitutes for vitreous bodies, tubes for intraocular transplantation and drug-sustained release agents for intraocular transplantation, which are used alone or in combination depending on the content of each particular ophthalmic operation.

Vitamin D (ergocalciferol or cholecalciferol) locally administered to the eyes controls the protein synthesis in the octivated cells in the intraocular tissues responding to the operative invasion, or it is replaced with hydroxyl group at one or both of the C1 position on the sterol A ring and the C25 position on the side chain by enzymatic reaction of mitochondria or microsomes in the intraocular cells to thus be converted into active vitamin D which exerts an influence on the deoxyribonucleic acid (DNA) of the activated cells to thus control the cellular activities.

In case of active vitamin D's, i.e., naturally occurring vitamin D derivatives or analogues, the local and direct administration thereof to the eyes can affect the DNA of the activated cells to thus control the differentiation induction or control the protein synthesis or the like.

The agent intraocularly administered for controlling the cellular activity in intraocular tissues may be prepared by incorporating oil-soluble vitamin D or active vitamin D into injections to be intraocularly administered, or admixed with, applied to, adhered to or embedded in, for instance, viscoelastic substances, intraocular lenses (or substitutes for crystalline lenses), substitutes for vitreous bodies, tubes for intraocular transplantation and drug-sustained release agents for intraocular transplantation. The agent intraocularly administered for controlling the cellular activities of intraocular tissues is intraocularly administered to mammals including man during ophthalmic operations to thus relieve any possible complications after the operations, which may leads to impaired vision.

The concentration of naturally occurring vitamin D in the agent intraocularly administered suitably ranges from about 1 μg/ml to 100 μg/ml for intraocular injections and viscoelastic substances, because the agent is in general locally administered. The vitamin D concentration in the intraocular implants and sustained release agents are not limited to the foregoing range. On the other hand, the concentration of active vitamin D suitably ranges from about 0.1 ng/ml to 10 μg/ml for intraocular injections and viscoelastic substances. The vitamin D concentration in the intraocular implants and sustained release agents are not limited to the foregoing range.

To demonstrate the usefulness of the present invention, the effect on the intraocular cells which respond to operative invasion, in particular, corneal endothelial cells and the lens epithelial cells were investigated with Japan white rabbits receiving the cataract surgery and keratotomy. The results of these tests indicate that the extent of the proliferation of the lens epithelial cells is low or the proliferation, migration as well as extension of the corneal endothelial cells are accelerated in the animals to which the aqueous agent intraocularly administered or the viscoelastic substance of the present invention was administered during the operations, as compared with the control group to which only the vehicle was administered. In other words, the results indicate that the administration thereof exerts a favorable influence on the visual power in the postoperative prognosis.

It could be confirmed, on the basis of these results, that the direct administration of of a vitamin D compound to the eyes during ophthalmic operations permits the control of the cellular activities in damaged intraocular tissues without any time lag.

Vitamin D and active vitamin D do not show any cytotoxicity so far as they are not used in an unreasonably high concentration and therefore, they would not adversely affect the normal cells.

Vitamin D, ergocalciferol, cholecalciferol or the like are converted into active vitamin D by the hydroxylase in intraocular cells which respond to operative invasion, in particular, cells which come in contact with the anterior and posterior chambers and the crystalline lenses, the resulting active vitamin D bind to the vitamin D-receptors of the foregoing cells per se or the cells in the proximity thereto, then incorporated into the nuclei thereof and exerts an influence on the DNA to thus control the differentiation induction or to control the production of, for instance, various cytokines or proteins. In other words, the intraocular cells, in particular, the epithelial and/or endothelial cells may serve not only as target cells for active vitamin D, but also as vitamin D-producing cells.

The agent intraocularly administered of the present invention is most preferably used in the form of an aqueous agent intraocularly administered. The ophthalmic viscoelastic substance is used in ophthalmic operations as an essential tool in order to, for instance, protect the intraocular tissues from the operative invasion and ensure the easiness of the operations. It has been known that the viscoelastic substance is removed from the eyes after the operation, but the agent remains in the eyes over about 3 to 7 days while being diluted, decomposed and absorbed therein. Thus, the incorporation of a vitamin D compound in the ophthalmic viscoelastic substance and the use thereof in, for instance, the cataract surgery and intraocular lens-transplantation would achieve excellent outcomes in controlling the cellular activities such as the corneal endothelial cells and the lens epithelial cells which face the anterior and posterior chambers and the lens capsules. In case of the intraocular lens-transplantation, vitamin D is coated on, adhered to or embedded in the intraocular lens to thus control the cellular activities of the intraocular tissues, in particular, the lens epithelial cells which come in contact with the lens by the action of the vitamin D. Thus, the transparency of the lens capsules and the intraocular lenses can be ensured. In case of the substitute for vitreous bodies, controlled is the activity of cells, in particular, retinal glial cells which come in contact with the substitute for vitreous bodies in which a vitamin D compound is incorporated or embedded and thus any impaired vision caused due to the retinal cell-proliferation or retinodialysis can be relieved. In case of the tube for intraocular transplantation which is used in operations for glaucoma and those for lacrimal duct diseases, controlled is the activity of cells which come in contact with the tube for intraocular transplantation in which a vitamin D compound is incorporated or embedded or to which a vitamin D compound is coated and thus, any scar formation due to proliferation of the cells can be suppressed. In case of the drug-sustained release agent to be intraocular transplanted, a vitamin D compound is gradually released from a drug-sustained release agent in which the vitamin D compound is incorporated or embedded to control the neighbouring cells and to thus suppress hyperplasia of cells or excess production of cellular materials. When transplanting the drug-sustained release agent to be intraocular transplanted in the conjunctival sac, the vitamin D compound released from the sustained release agent permeates through the cornea to thus control cellular activities in intraocular tissues.

There have mainly been used, as anti-inflammatory agents, pharmaceutical preparations of adenocorticosteroids, but these preparations may cause, as ophthalmologic side-effects, steroid glaucoma, steroid cataract, and mycotic infection and accordingly, there has been a tendency of avoiding or reducing the use of such steroid preparations.

When orally administering a large amount of the conventional pharmaceutical preparations of vitamin D and/or active vitamin D, there is observed hypervitaminosis D, in which calcium and phosphoric acid contents in the blood increase and which is accompanied by the calcification of soft tissues such as kidney, artery, smooth muscle and lung. The provitamin D, previtamin D, vitamin D, active vitamin D, active vitamin D analogues, vitamin K or vitamin K analogues used as effective components in the present invention can show desired effects in an amount smaller than that conventionally used and no side-effects would be recognized even when the effective components are penetrated into the blood through the skin, conjunctiva and/or cornea. In addition, the vitamin D compound used in the intraocularly administered agent of the present invention can show its effect even when it is administered only one time during an operation and thus no side-effects would be recognized even when the whole amount of the compound administered is entered into the blood.

The present invention will hereinafter be described in more detail with reference to the following Preparation Examples and Test Examples.

PREPARATION EXAMPLE 1

Vitamin D stock solution (cholecalciferol 10 mg/ml of ethanol) was diluted 100 times with ethanol, followed by further diluting the resulting dilute solution 100 times with Polysolbate 80 Eye Drop Solution (comprising a 0.1:100 (v/v) mixture of Polysolbate 80 and ophthalmic physiological saline), as a solvent to thus give an ophthalmic composition having a vitamin D concentration of 1 μg/ml.

PREPARATION EXAMPLE 2

Active vitamin D stock solution (calcitriol, 1α, 25-dihydroxy vitamin D 10 mg/ml of ethanol) was diluted 100 times with ethanol, followed by further diluting the resulting dilute solution 100 times with a medium-chain fatty acid (triglyceride) to thus give an ophthalmic composition having an active vitamin D concentration of 1 μg/ml.

PREPARATION EXAMPLE 3

Vitamin D stock solution (cholecalciferol 10 mg/ml of ethanol) was diluted 100 times with ethanol, followed by further diluting the resulting dilute solution 100 times with an oil base for ophthalmological use consisting of purified sesame oil to thus give an ophthalmic composition (a UV screening agent) having a vitamin D concentration of 5 μg/ml.

PREPARATION EXAMPLE 4

Vitamin $K_2$ (menaquinone; molecular weight: 444.7 dalton) was diluted 100 times with ethanol, followed by further diluting the resulting dilute solution 100 times with an oil base for ophthalmological use consisting of purified sesame oil to thus give an ophthalmic composition (a UV screening agent) having a vitamin $K_2$ concentration of 5 μg/ml.

PREPARATION EXAMPLE 5

Active vitamin D stock solution (calcitriol, 1α, 25-dihydroxy vitamin D; 10 mg/ml of ethanol) was diluted 10 times with ethanol, followed by further diluting the resulting dilute solution 100 times with a medium-chain fatty acid (triglyceride) to thus give a UV screening agent having an active vitamin D concentration of 10 μg/ml.

PREPARATION EXAMPLE 6

Vitamin D (cholecalciferol; 5 mg) was dissolved in 100 g of propylene glycol to thus give a UV screening agent having a vitamin D concentration of 50 μg/g.

PREPARATION EXAMPLE 7

Vitamin D (cholecalciferol; molecular weight: 384.6; 1 mg) was dissolved in 10 ml of ethanol (purity: 99.9%), followed by further diluting 0.1 ml of the resulting dilute solution 100 times with Polysolbate 80 Eye Drop Solution (0.1% Tween 80-containing ophthalmic physiological saline), as a solvent to give an ophthalmic anti-allergic agent having a vitamin D concentration of 1 μg/ml.

PREPARATION EXAMPLE 8

Active vitamin D (calcitriol: 1 α, 25-dihydroxy cholecalciferol; 0.1 mg) was dissolved in 100 ml of ethanol (purity: 99.9%), followed by further diluting 0.1 ml of the resulting solution 100 times with Polysolbate 80 Eye Drop Solution (0.1% Tween 80-containing ophthalmic physiological saline) to give an ophthalmic anti-allergic agent having an active vitamin D concentration of 10 ng/ml.

PREPARATION EXAMPLE 9

Active vitamin D (calcitriol; 100 μg) was dissolved in 10 ml of ethanol (purity: 99.9%), followed by further diluting 1 ml of the resulting dilute solution 100 times with Polysolbate 80 Eye Drop Solution (0.1% Tween 80-containing ophthalmic physiological saline) to give an agent intraocularly administered having an active vitamin D concentration of 0.1 μg/ml. The ophthalmic aqueous solution used herein was a solution of 780 mg of sodium chloride and 153 mg of potassium chloride in 100 ml of distilled water for injections whose pH value was adjusted to 7.4 using sodium hydroxide. The osmotic pressures of the agent intraocularly administered and the ophthalmic aqueous solution were adjusted to 280 mOsm.

PREPARATION EXAMPLE 10

Active vitamin D (1 α, 25-dihydroxy cholecalciferol; 100 μg) was dissolved in 10 ml of ethanol (purity: 99.9%), followed by further diluting and mixing 14 μl of the resulting dilute solution 100 times with 2 bials of a sodium hyaluronate aqueous solution (0.7 ml of a 1% sodium hyaluronate aqueous solution/bial; available from Santen Pharmaceutical Co., Ltd.), as a solvent to give an agent intraocularly administered having an active vitamin D concentration of 0.1 μg/ml.

TEST EXAMPLE 1

In this test, 4 Japan white rabbits weighing a body weight of 2 kg were used. After anesthetized, a partial thickness incision to a depth of a half thickness of the cornea on the right eye was made with a 5 mm trephine, and the resulting circular flap including corneal epitherium and stroma was dissected by a razor blade. The left eye remained untreated (or was free of any operation). After the operation mentioned above, an ointment and an eye drop containing ofloxacin as an antibiotic agent were administered to the right eyes of these four animals. Two out of these four animals constituted Group A and the remaining two animals constituted Group B.

The animals in group A were topically treated with 40 μl (about 2 drops) of the ophthalmic composition prepared in Preparation Example 1 for each time, three times daily at 4 hours intervals starting from one day after the treatment. On the other hand, the animals in group B were treated in a same manner in the group A, except the ophthalmic solution was replaced to polysolbate 80 eyedrop solution free of vitamin D. All of the operated eyes were inspected for the degree of corneal haze/opacity at one week, two weeks and one month after the operation under a slit-lamp microscope. The results were evaluated on the basis of the six stage criteria ranging from 0 (no haze) to 5 (total opacity).

All animals in Group A either Group B were judged as falling within the rank 0 one week after the operation.

Two weeks post operation, two eyes in Group B developed quite slight subepithelial haze which were evaluated as in the rank 1. One eye in Group A developed very slight subepitherial haze and was evaluated as being in the rank 1, but the other eye did not develop haze at all and accordingly, it was evaluated as in the rank 0. At one month after the operation, the eyes in group B developed haze which were evaluated as in the rank 3 and in the rank 1 respectively. One eye in group A developed haze being evaluated as in the rank 1 while the other eye did not develop haze at all.

In Test Example 1, there were not observed side-effects such as keratoleukoma caused by calcium deposition on the cornea possibly due to the administration of vitamin D, conjunctival hyperemia, fibrin-deposition within the anterior chamber and other intraocular disorders. It has been confirmed that the local administration of vitamin D to the eyes according to the present invention permits the inhibition of the activities of corneal epithelial cells and stromacells which are in inflammatory conditions and in the course of wound healing processes and the inhibition of the excess production of the cellular materials derived from these cells. Moreover, it has been suggested that vitamin D or active vitamin D should remain within the corneal tissues and the lacrimal fluid by the dropping of the ophthalmic composition of the invention in the eyes even when the corneal epithelium is dissected and this should result in the significant screening of detrimental ultraviolet rays. Moreover, the foregoing results also suggest that vitamin D may be an agent for treating corneal diseases such as keratitis, corneal ulcer and corneal degeneracy since vitamin D can inhibit the activities of the corneal epithelial cells and keratocytes and the excess production of the cellular materials by these cells. The results of the foregoing test also indicate that the ophthalmic composition of the present invention is also effective in man and is not detrimental to human bodies.

TEST EXAMPLE 2

In this Test Example, there was examined the effect of ultraviolet rays upon the eyes. Six Splague-Doly (SD) rats were used. Two out of these six rats constituted Group D (to which vitamin D was administered through dropping in the eyes), another pair of animals constituted Group K (to which vitamin $K_2$ was administered through dropping in the eyes) and the remaining two thereof constituted Group C (a control group). The ophthalmic composition prepared in Preparation Example 3 was dropped in the eyes of the animals in Group D (to which vitamin D was administered through dropping). The ophthalmic composition prepared in Preparation Example 4 was dropped in the eyes of the animals in Group K (to which vitamin $K_2$ was administered through dropping). The purified sesame oil for ophthalmic use was dropped in the eyes of the animals in Group C (control group). The dropping of each composition or sesame oil was carried out by dispensing 10 μl each of the composition or the sesame oil using a pipette and then dropping in the eye in an amount of one drop at a time. The dropping was carried out for both eyes, three times a day and was initiated one week before the ultraviolet irradiation. The step of irradiating ultraviolet rays was carried out in a commonly used UV sterilizer (wavelength of ultraviolet rays: 254 nm) and the animals were kept in this sterilizer.

Two days after the UV irradiation, there were observed slight spot-like superficial keratitis and chemosis on all of the eyes of the animals in Group C when observing them under a slit-lamp microscope. Very slight spot-like superficial keratitis was observed on all of the eyes of the animals in Groups D and K. Three days after the irradiation, severe spot-like superficial keratitis, chemosis and hydroblepharon were visible on all of the eyes of the animals in Group C, while slight spot-like superficial keratitis and chemosis were observed on all of the eyes of the animals in Groups D and K. The experiments for investigation of the effect of ultraviolet rays upon the eyes were terminated at this stage.

These results indicate that the effect of ultraviolet rays on the animals in Groups D and K is distinctly low compared with that observed for the animals in Group C and that the cornea, conjunctiva and eyelid of the former are protected from the action of ultraviolet rays. The foregoing experimental results clealy indicate that the ophthalmic composition (UV screening agent) of the present invention permits the protection of the eyes and the skin, for instance, cornea, conjunctiva and eyelid from the action of ultraviolet rays and that the ophthalmic composition of the present invention is also effective in man and is not detrimental to human bodies.

TEST EXAMPLE 3

Conjunctival allergy was induced in three Hartley guinea pigs by repeatedly subcutaneously injecting a mixture comprising equivalent amounts of a solution of ovalbumin (OVA) in physiological saline and Freund complete adjuvant in an amount of 0.5 ml per injection over three times at intervals of 2 weeks to thus sensitize these animals and then instilling 10 µl of an aqueous OVA-physiological saline solution in the both eyes after 10 days from the final injection. After 24 hours from the instillation, the cornea and conjunctiva were stained with rose bengal and the degree of the inflammation was observed under a slit-lamp microscope. After the microscopic observation, the animals were slaughtered, followed by excising the eye balls and preparation of the cornea and conjunctiva samples to thus subject the samples to histopathological observation. In this Test Example, the ophthalmic anti-allergic agent prepared in Preparation Example 7, the ophthalmic anti-allergic agent prepared in Preparation Example 8 or Polysolbate 80 Eye Drop Solution free of vitamin D was dropped in the both eyes of each animal, i.e., Subject A, Subject B or Subject C (control), respectively, three times a day (10 µl each) over the term extending from the initiation of the injection for sensitizing till the animals were slaughtered.

In the microscopic observation combined with the rose bengal under a slit-lamp microscope, the most severe conjunctival hyperemia was observed for Subject C and the degree thereof was reduced in the order, Subject A, Subject B and the conjunctival thickening was clearly observed on Subject C. The conjunctivas of the eyes were stained with rose bengal showing the sign of epithelial damage in all of the animals, but the lowest degree of staining was observed on Subject B.

The anterior clular tissue including bulbar conjunctiva were excised from each eye ball, followed by fixing in a Carnoa fixing solution for 4 hours, dehydration with ethanol, replacement to xylol, then embedding in paraffin, and slicing in sections of 4 µm thickness. These sections were stained with hematoxylin-eosin, Giiemsa's stain, immunohistochemical stain, and PAS stain respectively and then observed under a light microscope. As a result, it was found that the cell density observed in the specimens from Subject C was higher than that observed in Subject B. However, there was observed a discrepancy depending on the sites observed and accordingly, the comparison was carried out by determining approximate number of cells for each cell type (such as conjunctival epithelial cells, Goblet cells, mast cells, B cells, T cells and Langerhans' cells) on the specified 5 portions on each specimen and then obtaining each averaged value of 5 measurements. The total cell density observed for Subject C was about 1.6 time higher than that observed for Subject B. A number of epithelial cells detouched from the conjunctiva of Subject A was smaller than that of Subject C. However, a less extent of decrease in the number of inflammatory cell was observed in Subject A, than that observed in Subject B. From the foregoing facts, it would be believed that Subject C developed inflammation on the conjunctiva by the dropping of the allergy-inducing agent in the eyes, this leads to the increase in the cells and in turn the occurrence of allergic reactions. The number of mast cells observed for Subject B was lower than that observed for Subject C.

In this Test Example, there were not observed side-effects such as keratoleukoma caused by calcium deposition on the cornea possibly due to the administration of vitamin D or active vitamin D, conjunctival hyperemia, and intraocular diseases. The results of the foregoing test also indicate that the locally administered ophthalmic anti-allergic agent of the present invention is also effective in man and is not detrimental to human bodies.

TEST EXAMPLE 4

In vitro experiments were carried out for examining the effect of vitamin D upon epithelial cells of the porcine crystalline lenses.

A disc of 2 mm diameter was attached to the center of each Petri dish (two in all) and a mark was put on the back face of each Petri dish for enabling to locate the disc position, even after the disc was removed. The 3rd passage of the porcin lens epithelial cells were grown in the Petri dish till the cellular density reached about 90% of its maximum. And then, the disc was removed. To one Petri dish (D), there was added 2 ml of Eagle's modified medium supplemented with 10% calf serum containing 0.01 µM of active vitamin D (1 α, 25-dihydroxycholecalciferol, calcitriol) and cultured for seven days. To the other Petri dish (C) as a control, there was added the culture medium free of active vitamin D followed by cultivation thereof in the same manner.

When these Petri dishes were inspected at 1, 3, 5 and 7 days after the addition of vitamin D, it was found that a degree of the spreading of the lens epithelial cells into the region which had been covered with the disc was lower in the Petri dish containing active vitamin D than that in the control Petri dish. These Petri dishes were inspected for the rate (%) of the area occupied by cells, in the region from which the disc (diameter: 2 mm) was removed. As a result, the following results are obtained.

|  | Petri Dish (D) Pres. Inv. | Petri Dish (C) (Cont.) |
|---|---|---|
| 1 Day After the Initiation of Cultivation | 0 | 10 |
| 3 Days After the Initiation of Cultivation | 10 | 30 |
| 5 Days After the Initiation of Cultivation | 20 | 60 |
| 7 Days After the Initiation of Cultivation | 30 | 80 |

TEST EXAMPLE 5

The development of the opacity on the lens capsule following the cataract surgery was examined, using rabbits.

In this Test Example, six Japanese white rabbits weighing 2 kg were used. The right eye (to be operated) of each animal was subjected to mydriasis using a mydriatic. After being aresthetized, a perforating incision was carried out at the edge of the cornea in the direction of 12 o'clock, followed by filling the anterior chamber with a viscoelastic substance (1% aqueous solution of sodium hyaluronate) and excision of the anterior sac of the crystalline lens in a shape of a disc with a diameter of about 5 mm. Thereafter the punctured incision wound was widened to a width of about 3.0 mm, followed by sonically emulsifying and aspirating crystalline lenses to thus remove the lens nucleus and cortex lentis through aspiration. Three animals were randomly assigned to a drug-administered group in which about 1 ml of the agent intraocularly administered prepared in Preparation Example 10 was gradually injected through the anterior chamber so that the lens capsule of lens and the anterior and posterior ocular chambers were filled with the agent. On the other hand, the remaining three animals constituted a control group in which a 1% aqueous solution of sodium hyaluronate solution free of active vitamin D was injected in the same manner. The incised wounds on the cornea were closed by a single thread suture using 9-0 silk thread to thus finish the operation. An ointment and an eye drop containing ofloxacin as an antibiotic agent were administered to the operated eyes. After the operation, an antibiotic agent and a mydriatic were administered to the operated eyes, over 3 days, three times a day and one time a day, respectively.

Two animals were selected from each corresponding Group, i.e., drug-administered Group and control Group, which did not develop post operative disorders such as infection and/or pupillary adhesion and the selected four animals were inspected for the degree of turbidity developed on the posterior lens capsule after the operation. One week after the operation, each animal was subjected to mydriasis using a mydriatic and then the operated eyes were observed under a slit-lamp microscope. As a result, it was found that a band-like cloudy region was observed on all of the operated eyes at the peripheral edge of the region from which the anterior sac of the crystalline lens had been removed, that the extent of the cloudy region observed on the eyes of the drug-administered Group was more slight than that observed on the eyes of the control Group and that the width of the cloudy region observed on the eyes of the drug-administered Group was distinctly narrower than that observed on the eyes of the control Group. The degree of transparency of the posterior sac of the crystalline lens observed for the drug-administered Group was higher than that observed for the control Group.

TEST EXAMPLE 6

The degree of the corneal edema possibly developed after the perforating incision of the cornea was examined with rabbits.

In this Test Example, six Japanese white rabbits weighing 2 kg were used. The right eye (to be operated) of each animal was subjected to mydriasis using a mydriatic. After anesthetized, each rabbit received the penetrating incision in 3 mm width as forming a self sealing valve on the cornea of the right eye at the position of 12 o'clock about 4 mm apart from the centre of the pupil. Three animals extracted at random from these six animals constituted a drug-administered group in which about 1 ml of the intraocularly administered agent prepared in Preparation Example 9 was gradually injected into the anterior chamber so that about 1 ml of the aqueous humor of the anterior chamber was replaced therewith. On the other hand, the remaining three animals constituted a control group in which a Polysolbate 80 aqueous solution free of active vitamin D (0.1%-Tween 80 aqueous solution) was injected in the same manner. After the operation, an antibiotic agent and a mydriatic were administered to the operated eyes, over 2 days, three times a day and one time a day, respectively.

Seven days after the operation, each animal was subjected to mydriasis using a mydriatic and then the operated eyes thus anesthetized were observed under a slit-lamp microscope. As a result, it was found that incised wounds of the corneal epithelium, stroma and endothelium of all the three animals in the drug-administered Group showed transparency higher than that observed for the control Group and that the extent of the edema developed was also smaller than that of the latter. Each cornea was determined for the degree of astigmatism as measured at the position 2.5 mm apart from the center of the cornea using a corneal topology analyzer. As a result, it was found to be, on the average, about 7.7 diopters and 20.2 diopters for the drug-administered Group and the control Group, respectively. The foregoing findings concerning the cornea indicate that active vitamin D and calcitriol prevent the occurrence of turbid cornea and defective sight in a local region, i.e., in the eyes. In addition, these findings also suggest that the drug of the invention is strongly involved in the proliferation and migration of the corneal epithelial cells even if the drug is administered only once during the operation.

In Test Examples 5 and 6, there were not observed side-effects such as conjunctival hyperemia, fibrin-deposition within the anterior chamber, intraocular diseases and keratoleukoma caused by calcium deposition probably due to the administration of vitamin D. It has been confirmed that the local administration of vitamin D to the eyes according to the present invention permits the control of the cellular functions of conjunctiva, corneal epithelial cells, stroma and endothelial cells as well as epithelial cells of crystalline lens which are in inflammatory conditions and in the course of wound healing processes and the inhibition of the excess production of the cellular materials formed by these cells. The results of the foregoing tests also indicate that the ophthalmic agent to be administered during operations according to the present invention is also effective in man and is not detrimental to human bodies.

What is claimed is:

1. An ophthalmic composition for preventing corneal haze/opacity and corneal refraction anomaly observed after anterior ocular tissues are damaged or due to corneal diseases, which composition is in the form of aqueous eye drops, liposomes, microspheres, proteins, collagen, and soft contact lenses, which composition comprises:
   a) an effective amount of at least one compound selected from the group consisting of ergocalciferols and cholecalciferols; and
   b) an ophthalmically acceptable carrier.

2. An ophthalmic composition for protecting ocular tissues from harmful ultraviolet rays, which composition is in the form of aqueous eye drops, liposomes, microspheres, proteins, collagen, and soft contact lenses, which comprises:
   a) an effective amount of at least one compound selected from the group consisting of ergocalciferols, cholecalciferols, an active vitamin D having a hydroxyl group on one or both of the C1 position on the sterol A ring and the C25 position on the side chain, oxacalcitriol, calcipotriol and dihydrotachysterol; and
   b) an ophthalmically acceptable carrier.

3. The ophthalmic composition of claim 2, wherein the active vitamin D compound having a hydroxyl group on one or both of the C1 position on the sterol A ring and the C25 position on the side chain is a compound selected from the group consisting of calcitriol ($1\alpha$, 25-dihydroxy vitamin D), $1\alpha$, 24-dihydroxy vitamin D, $\alpha$-calcidol ($1\alpha$-monohydroxy vitamin D), calcifedol (25-monohydroxy vitamin D), $1\alpha$, 24, 25-trihydroxy vitamin D and $1\beta$, 25-dihydroxy vitamin D.

4. An ophthalmic composition for protecting the ocular tissues from harmful ultraviolet rays, which composition is in the form of aqueous eye drops, liposomes, microspheres, proteins, collagen, and soft contact lenses, which comprises:
   a) an effective amount of vitamin K; and
   b) an ophthalmically acceptable carrier.

5. A UV screening composition which is in the form of an ointment, lotion, cream or spray, which comprises:
   a) an effective amount of at least one compound selected from the group consisting of ergosterol, 7-dehydrocholesterol, pre-ergocalciferol, precholecalciferol, $1\alpha$, 24-dihydroxy vitamin D, $\alpha$-calcidol, calcifedol, $1\alpha$, 24, 25-trihydroxy vitamin D, $1\beta$, 25-dihydroxy vitamin D, oxacalcitriol, calcipotriol, dihydrotachysterol, vitamin $K_1$, vitamin $K_2$ and menadiol diphosphate; and
   b) a topically acceptable carrier.

6. An anti-allergic composition in the form of aqueous eye drops, which comprises:

a) an effective amount of at least one member selected from the group consisting of ergocalciferols, cholecalciferols, an active vitamin D compound having a hydroxyl group on one or both of the C1 position on the sterol A ring and the C25 position on the side chain, vitamin $D_2$ compounds, vitamin $D_3$ compounds, active vitamin $D_2$ compounds and active vitamin $D_3$ compounds; and b) an ophthalmically acceptable carrier.

7. The anti-allergic composition of claim 6, wherein the active vitamin D compound having a hydroxyl group on one or both of the C1 position on the side chain is selected from the group consisting of calcitriol (1α, 25-dihydroxy vitamin D), 1α, 24-dihydroxy vitamin D, α-calcidol (1α-monohydroxy vitamin D), calcifedol (25-monohydroxy vitamin D), 1α, 24, 25-trihydroxyvitamin D and 1β, 25-dihydroxy vitamin D.

8. A composition for controlling cellular activities of intraocular tissues during an ophthalmic operation, which comprises:

a) an effective amount of at least one member selected from the group consisting of ergocalciferols, cholecalciferols, active vitamin D compounds having a hydroxyl group an one or both of the of the C1 position on the sterol A ring and the C25 position on the side chain, vitamin $D_2$ compounds, vitamin $D_3$ compounds, active vitamin $D_2$ compounds and active vitamin $D_3$ compounds; and b) a carrier acceptable for intraocular administration.

9. The composition of claim 8, wherein said ophthalmic operation is selected from the group consisting of cataract operation, intraocular lens transplantation, operation for treating corneal disease, operation for correcting corneal refraction, operation for treating glaucoma, operation for treating ocular trauma, operation for treating lens-related disease, operation for restoring retina and operation for treating lacrimal duct-related diseases.

10. The composition of claim 8, wherein component a) is selected from the group consisting of calcitriol (1α, 25-dihydroxy vitamin D), 1α, 24-dihydroxy vitamin D, α-calcidol (1α-hydroxy vitamin D), calcifedol 25-monohydroxy vitamin D), 1α, 24, 25-trihydroxy vitamin D), 1β, 25-dihydroxy vitamin D, 22-oxacalcitriol, calcipotriol, KH 1060 and dihydrotachysterol.

11. The composition of claim 8, which is in a form selected form the gorup consisting of injections to be intraocularly administered, viscoelastic substances, intraocular lenses, substitutes for vitreous bodies, tubes for intraocular transplantation and drug-sustained release agents for intraocular transplantation.

* * * * *